United States Patent [19]

Harnick

[11] 4,243,038
[45] Jan. 6, 1981

[54] SKIN INCISING DEVICE FOR SCAR REMOVAL

[76] Inventor: Donn B. Harnick, 228 S. Barry Ave., Mamaroneck, N.Y. 10543

[21] Appl. No.: 23,291

[22] Filed: Mar. 23, 1979

[51] Int. Cl.³ .............................................. A61B 17/32
[52] U.S. Cl. ....................................... 128/305; 30/305
[58] Field of Search ..................... 128/305, 355, 316; 30/303, 304, 315, 314, 123; 7/158

[56] References Cited

U.S. PATENT DOCUMENTS

| | | | |
|---|---|---|---|
| 1,903,789 | 4/1933 | Michaels | 30/304 |
| 3,302,591 | 2/1967 | Schmidt | 30/304 X |
| 3,613,242 | 10/1971 | Hill et al. | 30/305 |

OTHER PUBLICATIONS

"The Strip Graft Method in Hair Transplantation" Charles Vallis pp. 389-402 *Skin Surgery*.

*Primary Examiner*—Robert W. Michell
*Assistant Examiner*—Michael H. Thaler
*Attorney, Agent, or Firm*—Watson, Leavenworth, Kelton & Taggart

[57] ABSTRACT

A skin incising device for scar removal is disclosed comprising a holder and a first cutting member having an elongated relatively thin blade element with a continuous cutting edge characterized by a plurality of transversely disposed corrugations, the said corrugations being generally triangular in cross-sectional profile with at least one corrugation being rectangular in cross-sectional profile, said cutting member mounted on said holder such that the cutting edge projects outwardly therefrom. Also disclosed, as preferred embodiments, are means to adjust the depth of the skin incision of the device and imprint means releasably fastened to the device to first imprint an image on the skin of the intended incision pattern. Finally, a method for removing scar tissue is also disclosed in the present specification.

13 Claims, 6 Drawing Figures

SKIN INCISING DEVICE FOR SCAR REMOVAL

BACKGROUND OF THE INVENTION

1. Field of the Invention

This invention pertains to the field of skin incising devices. More particularly, the present invention is directed to a skin incising device applicable to the removal of scar tissue.

2. Description of the Prior Art

It is well-known in the art of plastic surgery that undesirable scar tissue can be removed for cosmetic purposes or otherwise. In removing the scar tissue, superficial skin incisions are made on each side of the scar, the scar tissue removed and the incised skin sutured such that there is produced a finer, less pronounced, scar and/or a scar which, by optical illusion (created by the particular pattern of the incision made in removing the original scar tissue), is actually camouflaged and barely visible.

The particular incision pattern which has been found by plastic surgeons to be most effective in producing this optical illusion effect is comprised of a continuous geometric design including a plurality of triangular shapes having interspersed therebetween a number of rectangular shapes.

In particular, the technique for scar removal that is generally being employed by plastic surgeons consists of first making a freehand drawing of the incisin pattern onto the patient's skin, employing a sterile marking device, on each side of the scar to be removed. The pattern drawn on one side of the scar must be substantially identical, parallel, and aligned with the pattern drawn on the other side of the scar.

The surgeon then proceeds to freehandedly make a superficial skin incision using an ordinary scalpel along the incision pattern he has just drawn. The incision depth is determined merely by "feel" based on the surgeon's experience.

After the required incisions have been made along both sides of the scar, the scar tissue layer is removed by means of forceps, the incised skin is undermined, usually with curved scissors to allow for easy closing, and then sutured together.

It has been determined that it takes the surgeon approximately one hour for every one inch of scar tissue to perform the above-noted scar removal procedure.

It is readily apparent that the procedure set forth above has many inherent problems and disadvantages.

Firstly, the procedure is very slow and time consuming and consequently, very costly to the patient. More importantly, however, is the fact that it is not exact and is greatly subject to human error. Thus, the initial incision patterns are drawn freehand and do not necessarily accurately reflect the actual design pattern desired. Moreover, as was noted above, two essentially identical patterns are to be drawn on both sides of the scar respectively. Each pattern must align and be parallel with the other. It is readily appreciated that such a requirement is indeed difficult to obtain when the incision patterns are drawn freehandedly.

Additionally, inasmuch as the actual incisions are also performed by hand with a scalpel, they generally do not accurately reflect the incision pattern drawn on the skin nor are they generally exact replicas of one another as they should ideally be.

Furthermore, the depth of the incision made is also not uniform throughout the entire incision. Too deep an incision results in extraneous bleeding which obscures and can even obliterate the working field and the pattern itself. Alternatively, too shallow an incision does not allow for the proper removal of the scar tissue.

SUMMARY OF THE INVENTION

Applicant has devised a new skin incising device which not only avoids substantially all of the above-noted disadvantages associated with the procedure generally being performed by plastic surgeons for scar tissue removal, but additionally, provides, as preferred embodiments, adjustable means for controlling the depth of the incision made, means for making an imprint of the desired incision patterns simultaneously and means for making both required incisions simultaneously.

In particular, the present invention is directed to a skin incising device for scar removal comprising a holder and a first cutting member having an elongated relatively thin blade with a continuous cutting edge characterized by a plurality of transversely disposed corrugations, the said corrugations being generally triangular in cross-sectional profile with at least one corrugation being rectangular in cross-sectional profile. The cutting member is mounted on the holder such that the cutting edge projects outwardly therefrom.

Thus, in its simplest form, the present invention comprises a device wherein a blade member is fashioned to the particularly desired incision pattern required by plastic surgeons and affixed to a holding device such that the entire incision can be made on the patient by placing the cutting device at the point where the incision is to be made and applying pressure to obtain the necessary incision. The blade is affixed to the holding device such that it is exposed only to a preselected height which is substantially equal to the required depth of incision. Consequently, by means of the skin incising device of the present invention, in just one quick step, the surgeon can obtain the required superficial incisions in the required incision pattern and at the required depth.

Two such devices can be joined together, being appropriately spaced apart, such that both of the required incisions can be made simultaneously, or alternatively, one holder can include two blade members parallelly spaced apart and aligned with each other to enable the simultaneous incisions to be made.

Additionally, in a preferred embodiment of the present invention, a removable imprint means for transferring a substantially identical image of the incision pattern onto the patient's skin prior to actual incision is also provided. In this embodiment, one or both of the required incision patterns can be "stamped" onto the patient at the scar site to provide the physician with an accurate and easily obtainable representation of the desired incision pattern and to pinpoint the exact location for the subsequent incision step.

In yet another preferred embodiment of the present invention, means are provided, if desired, for adjusting the depth of the incision made to suit the individual particular needs of a patient and/or to take into account the scar's location.

The technique generally being employed by plastic surgeons to remove scars which comprise freehandedly drawing the incision patterns and then freehandedly making the necessary incisions with a scalpel can be greatly improved and made more efficient and economical by the skin incising device of the present invention. Thus, the device of the present invention provides an imprint means for imprinting or stamping one or both of the desired incision patterns in just one quick step. The imprinted pattern, essentially perfectly aligned and parallelly spaced apart, can be imprinted in a matter of seconds in contrast to the present freehand technique which takes a substantially longer time and yet does not produce the results that are obtainable by the device of the present invention. Additionally, by means of the skin incising device of the present invention, the required incisions can be made in just one quick, easy step, to the required depth, and can be made simultaneously, greatly reducing the time required for making these incisions by hand and concurrently therewith, making incisions which are uniform in depth and accurately reflect the required incision pattern.

By employing the device of the present invention, a plastic surgeon can reduce the time required for the removal of scar tissue from an average of about one hour per inch of scar tissue to about 0.3 hours per inch of scar tissue or, said another way, presents a timesaving of about 60% and correspondingly, makes the physician that much more efficient.

In an article entitled "The Strip Graft Method in Hair Transplantation" by Charles P. Vallis, page 389–402 of *Skin Surgery*, published Charles C. Thomas, Springfield, Ill. (1977), a device is disclosed which is employed for making an incision on the scalp for obtaining strip grafts for hair transplantation. The device employs a "running-W" razor blade which is fused to a plastic holder. The angle of each of the triangles contained within this "running-W" pattern must be 90°.

This strip graft "running-W" device, although somewhat related to the most simplest form of the present invention, is nevertheless quite remote therefrom. In particular, whereas the running-W device is intended for incising the scalp to obtain a strip graft for hair transplantation, the device of the present invention is specifically directed to scar removal which scars are generally located on parts other than the scalp area. Moreover, inasmuch as the running-W device is disclosed as being used for hair transtransplantation, i.e., incision of the scalp, there is no means for controlling the depth of the incision inasmuch as the physician merely incises the scalp until he reaches the skull. This is in contrast to the device of the present invention which does indeed have a means for controlling the depth of the incision and additionally, in a preferred embodiment, also provides an adjustable means for controlling such depth.

Additionally, whereas the device of the present invention provides, if desired, an imprint means for imprinting the desired incision pattern onto the patient prior to making the incision, no such imprinting means, in conjunction with the running-W device, is contemplated by Charles P. Vallis.

Finally, the running-W incision pattern employed in the strip graft hair transplantation procedure is not generally desirable for the removal of scar tissue for cosmetic purposes. Not only is the incision pattern not the same as that required by the present invention for scar removal, but in addition, as mentioned earlier, there is no means for controlling the depth of the incision which is in contrast to the skin incising device of the present invention.

DESCRIPTION OF THE PREFERRED EMBODIMENTS

Figure 1:
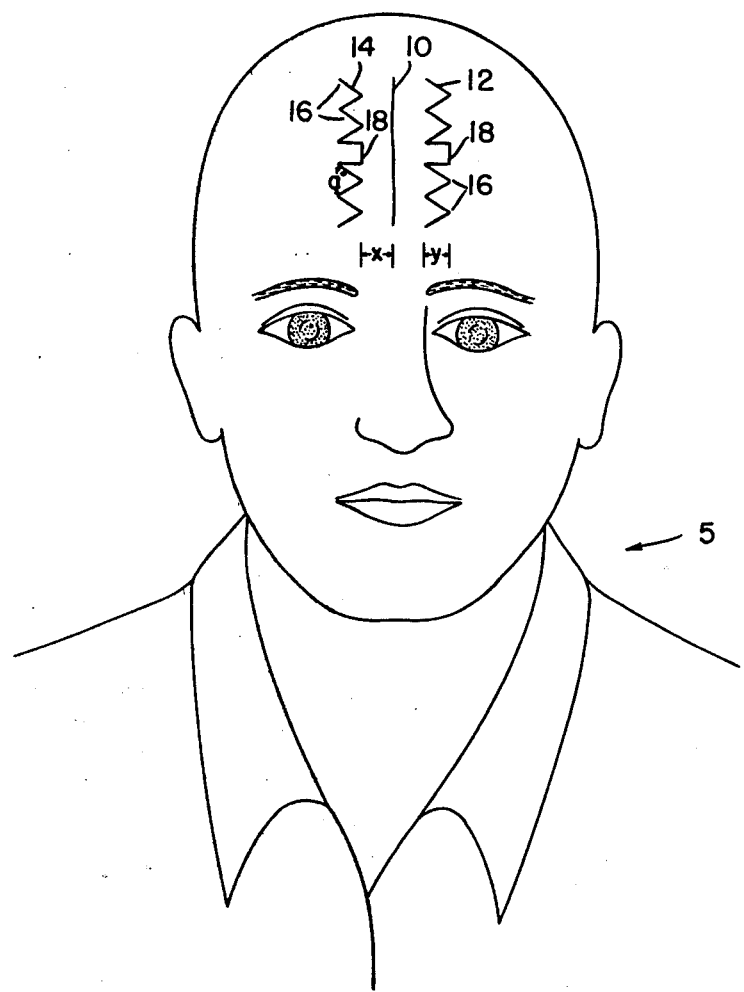
FIG. 1 is a front view drawing of a patient having a forehead scar, on each side of which there is depicted an identical, parallelly spaced, aligned incision design pattern which is employed in removing the scar for cosmetic purposes.

The same reference numerals are used throughout the Figures to indicate like elements.

Referring to FIG. 1, patient 5 is shown having a scar 10 which is to be removed for whatever purpose, generally, for cosmetic reasons. Although the device and method of the present invention is applicable to a scar located anywhere on the human body, it is particularly applicable to scars found on the head and neck area where for cosmetic purposes, these scars are to be removed.

To remove the scar tissue 10 such that the resulting scar (not shown) is optically "hidden" or "camouflaged", it is necessary to make superficial incisions of the skin along each side of the scar in a particular incision pattern such as shown in FIG. 1 as incision patterns 12 and 14. Incisions made in such a pattern have been found to be effective in producing the desired optical illusion effect and comprise a continuous geometric design including a plurality of triangular shapes 16 having interspersed therebetween a number of rectangular shapes 18.

There is no criticality as to the specific incision pattern employed as long as it is comprised of a geometric pattern having a plurality of triangular shapes interspersed with rectangular shapes. Plastic surgeons have determined that a haphazard arrangement of a combination of triangular and rectangular shapes provide for the desire camouflaging effect of the resulting scar. The employment of such a geometrical incision pattern for scar removal, i.e., a continuous pattern of triangular shapes interspersed with a number of rectangular shapes, is well-known in the art.

Generally, the incisions are made such that the nearest points of the incision to scar tissue 10 are approximately 3 to 10 mm as shown by distance "X" in FIG. 1. Additionally, the width of the incision is generally about 3 to 6 mm, as shown as distance "Y" in FIG. 1. Angle "a°" of triangles 16 is generally about 30° to 60° and preferably about 60°. Desirably, the triangles are equilateral triangles having all sides equal and their angles at 60°.

The incision made on each side of the scar must be parallelly spaced apart, aligned and identical to one another such that after the scar has been removed, the incised skin can be interfitted along the design pattern and sutured together. By "interfitted", it is meant that, for example, rectangle 18 of incision 12 is placed in juxtaposition to rectangle 18 of incision 14. The triangular shapes of incision 12 are similarly placed in juxtaposition to their corresponding parts in incision 14, etc. In this manner, the resulting scar is similar in shape to the original incision design pattern thereby producing the desired optical effect.

Figure 2:
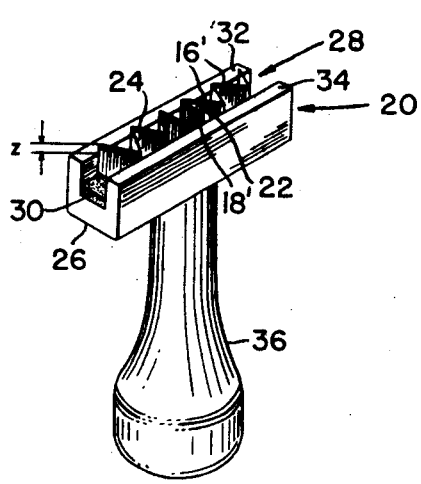
FIG. 2 is a perspective view of the skin incising device of the present invention in its most simplest form.

FIG. 2 depicts the simplest form of the skin incising device of the present invention. Cutter assembly 20 is comprised of a cutting member 22 having a cutting edge 24 and a holder 26 on which cutting member 22 is mounted.

Cutting member 22 is an elongated relatively thin blade element with a continuous cutting edge 24 having a plurality of transversely disposed corrugations being generally triangular in cross-sectional profile as shown by 16' in FIG. 2 and having at least one corrugation which is rectangular in shape as shown by 18'. The corrugations form a desired incision design pattern such as, for example, the incision design pattern 12 or 14 shown in FIG. 1 where the rectangular shapes 18 and the triangular shapes 16 of the incision pattern correspond to the rectangular shaped corrugation 18' and triangular shaped corrugation 16' of cutting member 22, respectively. As noted above, it is not critical to the present invention that the incision design pattern of cutting member 22 be in the exact pattern depicted in either FIGS. 1 or 2. Any incision pattern which is well-known to those skilled in the art for cosmetically removing scar tissue is equally as applicable and cutting member 22 can be modified accordingly.

Cutting member 22 can be mounted on holder 26 in any conventional manner which is well-known to one skilled in the art. In FIG. 2, a longitudinal slot 28 is provided in holder 26 for receiving cutting member 22 such that cutting edge 24 extends outwardly therefrom. The cutting member is desirably securely fastened within slot 28 of holder 26 by embedding the cutting member in plastic resin 30 or any other conventional resin or adhesive means well-known to the skilled art worker.

Cutting member 22 extends outwardly from slot 28 a distance "Z" above substantially planar surfaces 32 and 34. The height "Z" is preferably equal to the desired depth of the subsequent skin incision where top surfaces 32 and 34 act as a stopping means by abutting against the skin during the actual incision thereby preventing the cutting member from penetrating the skin to a depth greater than distance "Z". Generally, distance "Z", which corresponds to the desired depth of incision, and is the exposed height of cutting member 22, is in the range of from 0.25 to 4 mm. The depth of incision is such that only a superficial skin incision is made, usually cutting only the eperdermis layer.

The skin incising device may be employed by grasping holder 26 directly, or alternatively, a handle 36 can be optionally provided where the handle projects outwardly from holder 26. It is understood, of course, that any desirable handle means can be provided which is conventional in the art.

In use, the device of FIG. 2 would desirably be employed after the physician has drawn a rough freehand sketch of the pattern along each side of the scar to be removed in order to provide a general location for the incision site. It is understood that the exact incision design pattern need not be drawn on the patient for it is already inherently present in the skin incising device of the present invention itself. After the general area for incision has been marked off on the patient, the physician then grasps the skin incising device of the present invention, places cutting edge 24 against the skin at the desired point of incision and applies even hand pressure to force cutting edge 24 to cut through the skin to a depth automatically controlled by the exposed height of the cutting member. Consequently, in just one quick, easy step, the physician has obtained the entire required incision and to the required depth as well. The physician then repeats the procedure for the incision that is to be made on the opposite side of the scar.

Figure 3:
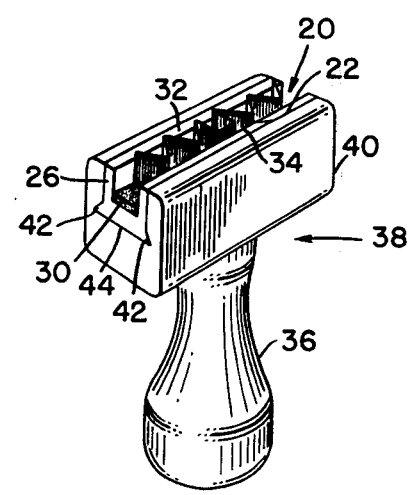
FIG. 3 is a perspective view of another embodiment of the present invention in which the cutting assembly is removable.

Referring to FIG. 3, there is shown another embodiment of the present invention wherein cutter assembly 20 is shown to be removable from handle member 38 which is comprised of handle 36 and fastening means 40. As can be seen from FIG. 3, the cutter assembly 20 is essentially the same as the cutter assembly shown in FIG. 2. Thus, cutting member 22 is once again recessed in longitudinal slot 28 of holder 26 and is permanently secured therein by resin 30. However, in the embodiment shown in FIG. 3, the bottom surface of holder 26 is provided with dovetail projections 42 which are complementary in shape to dovetail grooves 44 contained in fastening means 40 which in turn telescope over holder 26.

Figure 4:
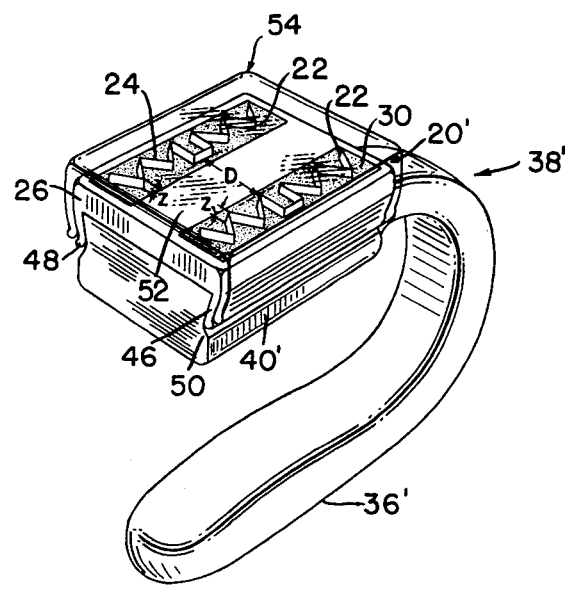
FIG. 4 is a perspective view of yet another embodiment of the present invention in which two identical cutting members are affixed to a removable cutting assembly. The cutting members are aligned with each other and parallelly spaced apart. This embodiment also comprises a removable protective cover and a handle means different from those depicted in either FIGS. 2 or 3.

The specific fastening means of the cutter assembly to the handle member is not critical to the present invention. Any conventional releasable fastening means may be employed. Thus, it is possible to provide holder 26 with dovetail grooves and provide fastening means 40 with corresponding complementary projections. Alternatively, as shown in FIG. 4, for example, a fastening means may be employed which comprises a skirt 46 extending at least from a portion of the periphery of cutter assembly 20' where skirt 46 is provided with an internal rim 48 interfitting with groove 50 located on fastening means 40' so that the cutter assembly is releasably secured to handle member 38' in a snap-on manner. If desirable, the location of the groove and corresponding rim can be reversed (not shown) so that there is a skirt projecting upwardly from fastening means 40' where the skirt is provided with a rim which interfits with a groove located on cutter assembly 20'.

The ability to be able to remove the cutter assembly as shown in the devices of FIGS. 3 and 4 is desirable for many reasons. In particular, where the device is to be disposed after use, it is more economical to simply dispose the cutter assembly itself rather than the entire device. Additionally, it is also possible to retain one handle member and simply change the cutter assembly as required in order to meet the specific needs of particular design patterns and/or incision depths.

FIG. 4 represents yet another embodiment of the present invention which provides for additional features not found in the devices shown in FIGS. 2 and 3. Particularly, as was discussed above, the device comprises a handle member 38' which includes a curved handle 36' and a fastening means 40'. Cutter assembly 20' is now provided with two cutting members 22. These cutting members are permanently mounted on holder 26 by resin 30 and are in aligned, parallelly-spaced apart relationship to one another. One cutting member is identical to the other and both cutting members extend from surface 52 a distance "Z" equal to the desired depth of incision. The distance "D" between the nearest points of the cutting members is approximately equal to twice the distance "X" shown in FIG. 1. Generally, this distance is about 6 to 20 mm.

Accordingly, by means of the device shown in FIG. 4, a physician is now able to make both required incisions simultaneously in just one simple step. The two incisions made by the device of FIG. 4 will be essentially identical, properly spaced apart, aligned, and incised to the desired depth.

Also shown in FIG. 4 is a protective cover 54 which is releasably fastened to holder 26 in the same manner that the cutter assembly 20' is releasably fastened to fastening means 40'. The protective cover 54 serves to protect the cutting member from accidental nicking and the like and also protects the user from accidental cutting until ready for use. Any type of protective cover may be employed where desired, the selection and design of which is well within the knowledge of one skilled in the art.

Figure 5:
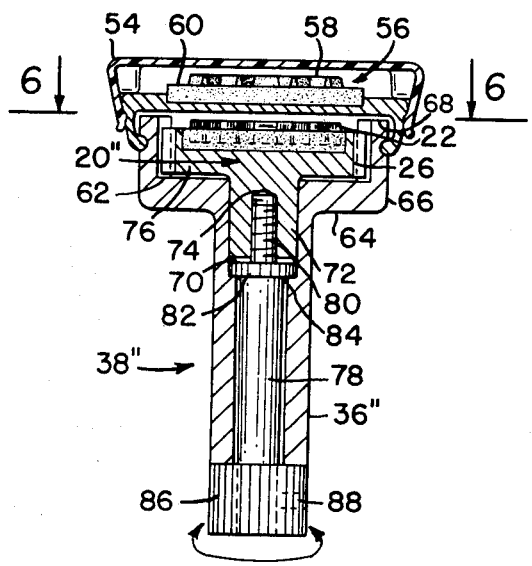
FIG. 5 is a cross-sectional front view of still another embodiment of the present invention which provides a means for adjusting the height of the cutting member to control the depth of incision.
Figure 6:
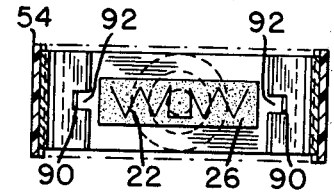
FIG. 6 is a cross-sectional top view taken along lines 6—6 of FIG. 5.

FIGS. 5 and 6 set forth still another embodiment of the present invention containing additional features not shown in the embodiments set forth in FIGS. 2, 3 or 4.

In this embodiment, the height of the exposed cutting member 22 is manually adjustable to set the depth of incision to any desired dimension. Additionally, in lieu of freehandedly drawing the incision pattern on the patient to locate the exact incision site, the embodiment shown in FIG. 5 also is provided with an imprint means 56 which includes a stamp 58 affixed to a base 60. The imprint means allows the physician to transfer a substantially identical image of the desired incision pattern directly onto the patient to provide the incision site for the subsequent incision. This is done by merely "stamping" the particular pattern onto the patient in one quick step.

More particularly, the adjustable skin incising device shown in FIGS. 5 and 6 include a handle member 38" which has a top surface 62 and a bottom surface 64. Projecting upwardly from a portion of the periphery of top surface 62 is skirt 66 which terminates in skirt edge 68. Projecting downwardly from bottom surface 64 is handle 36" which has contained therein bore 70.

Bore 70 extends entirely through handle 36" and continues on through bottom surface 64 and top surface 62.

Holder 26 has mounted thereon cutting member 22 in the same manner as described above in connection with the devices shown in FIGS. 2-4. In this embodiment, holder 26 is provided with a projection 72 which contains a cavity 74 provided with internal threads. Projection 72 is cylindrically shaped to complement and interfit with bore 70 as shown. The holder is positioned so that bore 70 telescopes over projection 72 and bottom surface 76 of the holder is juxtaposed to top surface 62 of the handle member.

Bore 70 houses a rotatable, translationally-fixed screw member 78 which is provided with external threads 80 to engage with the internal threads of cavity 74. Screw member 78 is provided with a collar 82 which rests on annular rim 84 of bore 70.

Additionally, knurled knob 86 is releasably attached to screw member 78 by locking pin 88 (shown in phantom lines). By rotating knurled knob 86, cutting assembly 20" will be displaced in an upward or downward direction, i.e., along the longitudinal axis of bore 70, depending on the direction of rotation of knob 86. Screw member 78 will be translationally fixed in its position, i.e., will not be displaced along its longitudinal axis, due to the combined restraining effects of collar 82 and knob 86 which is juxtaposed to the bottom surface of handle 36" as shown in FIG. 5.

If desired, indicia may be imprinted (not shown) on the knurled knob and/or the lower portion of handle 36" such that the extent of translational displacement of the cutter assembly along the longitudinal axis of bore 70 for a corresponding number of revolutions made with knob 86 can easily be determined.

By being able to adjust the height that cutting member 22 extends above skirt edge 68, the depth of the subsequent skin incision is controlled to meet the needs of a particular patient without the necessity of seeking a specific cutter assembly (such as those shown in FIGS. 2-4) which have the heights of their respective cutting members fixed to a particular incision depth.

To provide stability and to prevent lateral shifting and/or rotational movement of cutter assembly 20", guide means are provided which include grooves 90 located in the internal portion of skirt 66 and slidably, interfitted ribs 92 located on holder 26. It is understood, of course, that any guide means may be employed and the particular means for preventing rotational movement and providing stability of the cutter assembly is not critical to the present invention. Thus, for example, it is possible to provide holder 26 with grooves and skirt 66 with ribs (not shown) to accomplish the same objective. Different types of guide means are well-known to those skilled in the art.

Imprint means 56 is releasably fastened to skirt 66 of handle member 38" by any conventional fastening means. In FIG. 5, the fastening means shown in the snap-on arrangement described in connection with the device shown in FIG. 4 consisting of a rim and groove type arrangement.

In turn, releasably fastened to imprint means 56 is protective cover 54 which prevents accidental damage to stamp 58. Protective cover 54 is releasably fastened in the same manner as described above in connection with the device shown in FIG. 4.

Any releasable fastening means may be employed in the present invention for the cutter assembly, the imprint means, or the protective cover. Such fastening means are conventional and known to the skilled art worker.

Although FIG. 6 depicts only one cutting member 22 present, this is merely for the sake of clarity, and it is most preferable to provide two cutting members as well as an imprint means being capable of imprinting both incision design patterns simultaneously which are aligned and parallelly spaced apart to the desired distance, respectively.

Moreover, none of the features described in any of the various embodiments shown in FIGS. 2-6 need be limited to that particular embodiment. Thus, protective cover 54 may be employed with the embodiments shown in FIGS. 2 or 3. Similarly, releasable imprint means may also be employed in conjunction with the embodiments shown in FIGS. 2 to 4 and is not limited only to the embodiment shown and discussed in FIGS. 5 and 6. Interchangeability of the other features shown in the various embodiments are, of course, also possible.

In using the device shown in FIGS. 5 and 6, for example, the physician would first remove protective cover 54 and then imprint the desired incision pattern onto the patient by means of imprint means 56. If the imprint means were provided with only one incision pattern, the physician would have to imprint the pattern twice on each side of the scar to be removed. Preferably, if the imprint means were provided with two identical incision patterns, parallelly spaced apart and aligned, the physician would then be able to imprint both required patterns simultaneously onto the patient in one simple step. Where desired, the stamp can be provided with a sterile ink already present on the surface which makes contact with the patient's skin, or alternatively, conventional stamp pads, which have been previously sterilized, may also be employed.

Imprint means 56 is then removed exposing the cutter assembly. The physician would then determine the depth of the required incision based on various factors. Generally, these factors include the location of the scar, the character of the patient's skin, the type of scar, and the like. After having determined the required depth of incision, if the device of FIG. 5 were being used, the physician would then simply rotate knob 86 until the cutting member is at the desired height. If the embodiments of FIGS. 2-4 were being employed, however, the physician would merely select a cutter assembly having mounted thereon a cutting member at the desired fixed height.

The physician would then place the cutting edge of the cutting member against the patient to coincide with the previous imprint made which locates the incision site and would then apply even hand pressure to force the cutting edge through the skin to obtain the superficial incision in the preselected design pattern and to the desired depth. If the embodiment shown in FIG. 5 were being employed, skirt edges 68 would be the stopping means which abut against the skin and prevent incision greater than that portion of cutting member 22 which extends past skirt edge 68. Similarly, surfaces 32, 34 and 52 described in connection with the embodiments shown in FIGS. 2-4 also serve the same stopping purpose and will abut against the patient's skin to control the depth of incision.

If only one cutting member were provided on the cutter assembly, such as shown in FIG. 6, the physician would have to repeat the incision step. Preferably, however, two cutting members are provided such that both incisions can be obtained simultaneously in one step.

The incised scar tissue is then removed and the skin adjacent to the incisions is then undermined. The incised skin is then abutted together along the incision pattern so that the geometric shapes of the pattern interfit and is then sutured together.

The device of the present invention is not limited to the material of constructin of any of the components discussed hereinabove. Thus, the components may be comprised of wood, plastic, china, ceramic, glass, metal, etc. Combinations of these materials may also be employed. Of course, those skilled in the art will readily appreciate that a razor sharp metallic band would be most preferable for cutting member 22, for example, and that a rubber material would be most suitable for stamp 58. However, there is no criticality as to any of the materials employed. If certain components are to be sterilized after use as, for example, the handle member, it is desirable that it be composed of a material which readily lends itself to such a sterilization step. Similarly, if the cutter assembly is to be disposed after use, inexpensive material which would make such disposal economical would be most desirable. The selection of a particular type of material for a particular type of component which will be best suitable therefor is well within the knowledge of the ordinary skilled art worker.

As can be seen from the above description of the device of the present invention, a skin incising device is provided which is easy to use, greatly decreases the amount of time a plastic surgeon has to spend in removing scar tissue, and most importantly, has the distinct advantage of being able to provide simultaneous incisions which substantially reproduce a specific design pattern which are substantially aligned, parallelly spaced apart, and incised to a desired depth. It will readily be appreciated that a physician attempting to obtain the required incisions by means of a scalpel will generally not be able to duplicate the incisions that are possible by means of the skin incising device of the present invention.

Variations and modifications may be made without departing from the spirit and scope of the present invention.

Having thus described my invention, what I desire to secure by Letters Patent is:

1. A skin incising device for scar removal comprising:
   (a) a holder;
   (b) a first cutting member having an elongated relatively thin blade element with a continuous cutting edge characterized by a plurality of transversely disposed corrugations, the said corrugations being generally triangular in cross-sectional profile with at least one corrugation being rectangular in cross-sectional profile,
   said cutting member mounted on said holder such that the cutting edge projects outwardly therefrom; and
   (c) a removable imprint means for transferring at least one substantially identical image of the incision pattern produced by the transversely disposed corrugations of the cutting member and a releasabe fastening means for releasably fastening the imprint means to the holder.

2. The device of claim 1 wherein the holder has a substantially planar surface with a longitudinal slot therein for receiving the cutting member.

3. The device of claim 2 wherein the holder includes an integral projection extending outwardly to provide a handle whereby the holder can be securely grasped.

4. The device of claim 2 wherein the cutting member is recessed in said slot and extending outwardly from said surface a length equal to the desired depth of skin incision.

5. The device of claim 1 wherein a second cutting member having substantially the same corrugation configuration as the first cutting member is mounted on said holder in aligned, parallel-spaced apart relationship to the first cutting member.

6. The device of claim 5 wherein the cutting members are spaced apart in the range of from 6 to 20 mm.

7. The device of claim 1 wherein the angles formed by the triangular shaped corrugations are generally in the range of from about 30° to 60°.

8. An adjustable skin incising device for scar removal comprising:
   (a) a cutter assembly including i. a holder having a top and bottom portion, said bottom portion having a cavity provided with internal threads, ii. a cutting member having an elongated relatively thin blade element with a continuous cutting edge characterized by a plurality of transversely disposed corrugations being generally triangular in cross-sectional profile with at least one corrugation being rectangular in cross-sectional profile, said cutting member mounted on the top portion of said holder such that the cutting edge projects outwardly therefrom;

(b) a handle member having a top and bottom surface and a skirt terminating in a skirt edge extending upwardly from a substantial portion of the periphery of said top surface, said bottom surface having an integral projection extending outwardly therefrom to serve as a handle and includes a bore contained within the projection which extends through both the bottom and top surfaces of the member communicating and aligned with the cavity of the cutter asembly which is positioned such that the bottom portion of the assembly is juxtaposed to the top surface of the handle member, said bore housing a rotatable, translationally fixed screw member provided with external threads adapted to engage with the cavity internal threads of the cutter assembly wherein rotation of the screw member adjusts the relative height between the cutting edge of the cutting member and the skirt edge thereby controlling and adjusting the depth of skin incision; and (c) a removable imprint means for transferring a substantially identical image of the incision pattern produced by the transversely disposed corrugations of the cutting member and a releasable fastening means for releasably fastening the imprint means to the handle member.

9. The device of claim 8 further comprising a guide means for providing stability and preventing both lateral relative shifting and rotational movement of the cutter assembly.

10. The device of claim 9 wherein the guide means for providing stability and preventing both lateral relative shifting and rotational movement of the cutter assembly is comprised of at least one groove located on either the holder or the internal portion of the skirt and at least one slidably, interfitting rib located on either the holder or the skirt.

11. The device of claim 8 further comprising a removable protective cover member for said imprint means to prevent accidental damage thereof and a releasable fastener means for releasably fastening the protective cover to the said imprint means.

12. The device of claim 8 further comprising a removable protective cover member for said cutting member to prevent accidental cutting and/or damage to the cutting blade and a releasable fastener means for releasably fastening the protective cover to the handle member.

13. An adjustable skin incising device for scar removal comprising:

(a) a cutter assembly including
i. a holder having a top and bottom portion, said bottom portion having a cavity provided with internal threads, ii. a cutting member having an elongated relatively thin blade element with a continuous cutting edge characterized by a plurality of transversely disposed corrugations being generally triangular in cross-sectional profile with at least one corrugation being rectangular in cross-sectional profile, said cutting member mounted on the top portion of said holder such that the cutting edge projects outwardly therefrom;

(b) a handle member having a top and bottom surface and a skirt terminating in a skirt edge extending upwardly from a substantial portion of the periphery of said top surface, said bottom surface having an integral projection extending outwardly therefrom to serve as a handle and includes a bore contained within the projection which extends through both the bottom and top surfaces of the member communicating and aligned with the cavity of the cutter assembly which is positioned such that the bottom portion of the assembly is juxtaposed to the top surface of the handle member, said bore housing a rotatable, translationally fixed screw member provided with external threads adapted to engage with the cavity internal threads of the cutter assembly wherein rotation of the screw member adjusts the relative distance between the cutting edge of the cutting member and the skirt edge thereby controlling the depth of skin incision;

(c) a removable imprint means for transferring a substantially identical image of the incision pattern produced by the transversely disposed corrugations of the cutting member;

(d) a releasable fastening means for releasably fastening the imprint means to the holder; and (e) a removable protective cover member for said imprint means to prevent accidental damage thereof and a releasable fastener means for releasably fastening the protective cover to the imprint means.

* * * * *

UNITED STATES PATENT AND TRADEMARK OFFICE
CERTIFICATE OF CORRECTION

PATENT NO. : 4,243,038
DATED : January 6, 1981
INVENTOR(S) : Donn B. Harnick

It is certified that error appears in the above-identified patent and that said Letters Patent are hereby corrected as shown below:

```
Col. 1, line 48, "apparet" should read --apparent--.
Col. 2, line 65, "comprised" should read --comprises--.
Col. 3, line 27, "page" should read --pages--.
Col. 8, line 29, "of" should read --to--.
Col. 9, line 56, "constructin" should read --construction--.
Claim 8, Col. 11, line 24, "asembly" should read --assembly--.
```

Signed and Sealed this

Twenty-fourth Day of March 1981

[SEAL]

Attest:

RENE D. TEGTMEYER

Attesting Officer

Acting Commissioner of Patents and Trademarks